(12) United States Patent
Raz

(10) Patent No.: US 7,695,966 B2
(45) Date of Patent: Apr. 13, 2010

(54) METHOD FOR THE SEPARATION AND SORTING OF DIFFERENT BIOLOGICAL OBJECTS UTILIZING DIFFERENCES IN THEIR VISCOELASTIC PROPERTIES

(75) Inventor: Ryan Stephen Raz, Toronto (CA)

(73) Assignee: Canopus Bioscience Limited, Toronto, Ontario (CA)

( * ) Notice: Subject to any disclaimer, the term of this patent is extended or adjusted under 35 U.S.C. 154(b) by 550 days.

(21) Appl. No.: 11/334,303

(22) Filed: Jan. 18, 2006

(65) Prior Publication Data

US 2008/0160608 A1 Jul. 3, 2008

Related U.S. Application Data

(60) Provisional application No. 60/643,972, filed on Jan. 18, 2005.

(51) Int. Cl.
*C12N 5/02* (2006.01)
*C12N 15/85* (2006.01)
(52) U.S. Cl. ..................... 435/378; 435/325
(58) Field of Classification Search .................. None
See application file for complete search history.

(56) References Cited

U.S. PATENT DOCUMENTS 6,365,395 B1 * 4/2002 Antoniou ................ 435/239

OTHER PUBLICATIONS

Waugh, R. et al., "Surface area and volume changes during maturation of reticulocytes in the circulation of the baboon", J Lab Clin Med 129: 527-535 (1997).*
Peeters et al.; "Mechanical and failure properties of single attached cells under compression"; Journal of Biomechanics 38 (2005) 1685-1693.
Zhang et al..; "Mechanical properties of hepatocellular carcinoma cells"; World J Gastroenterol; 2002: 8(2):243-246.
Karcher et al..; "A Three-Dimensional Viscoelastic Model for Cell Deformation with Experimental Verification"; Biophysical Journal; vol. 85; Nov. 2003; 3336-3349.
Evans et al.; "Apparent viscosity and cortical tension of blood granulocytes determined by micropipet aspiration"; Biophysical Journal, vol. 56, 151-160 (1989), (Abstract only).
Peeters et al.; "Mechanical and failure properties of single attached cells under compression"; Journal of Biomechanics 38 (2005) 1685-1693.
Zhang et al..; "Mechanical properties of hepatocellular carcinoma cells"; World J Gastroenterol; 2002: 8(2):243-246.
Karcher et al.; "A Three-Dimensional Viscoelastic Model for Cell Deformation with Experimental Verification"; Biophysical Journal; vol. 85; Nov. 2003; 3336-3349.

* cited by examiner

*Primary Examiner*—Anand U Desai
(74) *Attorney, Agent, or Firm*—Foley & Lardner LLP

(57) ABSTRACT

A method for separating a multitude of biological objects by the type of the object. The method utilizes the differences in the viscoelastic properties for the different types of objects. As an example but not limited to: the method can be applied to most tumor cells that might be present in a sample of blood, allowing the tumor cells to be separated from the majority of the normal blood cells.

3 Claims, 7 Drawing Sheets

US 7,695,966 B2

METHOD FOR THE SEPARATION AND SORTING OF DIFFERENT BIOLOGICAL OBJECTS UTILIZING DIFFERENCES IN THEIR VISCOELASTIC PROPERTIES

CROSS-REFERENCE TO RELATED APPLICATIONS

This application claims the benefit of provisional patent application Ser. No. 60/643,972, filed Jan. 18, 2005 by the present inventor.

FEDERALLY SPONSORED RESEARCH

Not Applicable

SEQUENCE LISTING OR PROGRAM

Not Applicable

BACKGROUND OF THE INVENTION

1. Field of Invention

This invention relates to the separation of different types of biological objects.

2. Prior Art

It is often desirable to examine biological samples, and specimens for signs of abnormality and disease. A partial list of biological samples is bodily fluids such as blood, urine, and spinal fluids, Tissue, and tumor biopsies, water and soil samples, and plant tissues and fluids. Current practice is to search for and examine the biological objects of interest in the sample. A partial list of biological objects is cells, bacteria, viruses, and yeast. Within the sample there are usually a large number of biological objects of the same that are not of interest. It is therefore advantageous to separate and remove most of objects that are not of interest thus concentrating the objects of interest.

As an example, the cells in a sample of blood or spinal fluid might need to be examined for indications of cancer. Because these types of samples might well contain millions of cells, it is very advantageous to separate the majority cells and fluids that are not of interest, thus concentrating the cells of interest.

In blood and spinal fluids it is desirable to remove plasma, erythrocytes red blood cells, and leukocytes (white blood cells), thus concentrating the small number of cells that are not normally present and that might exhibit signs of abnormality such as cancer. As leukocytes are often very similar to the cells of interest it is difficult to remove these cells without losses. The resulting concentrated cells of interest are then used for further analysis.

Prior to the invention the main methods of separating cell types were: Separation by size, by centrifugation (density/specific gravity), and chemical properties.

Separation by size is usually done by filtering through a filter, or a array of one or more hollow tubes with a specific hole size. Cells that are larger then the hole stay on one side of the filter while smaller cells go through the filter and are collected on the other side of the filter. If the two types of cells have an overlapping size distribution (a certain portion of the cells of one type are larger while another portion are smaller then the other type of cell), then the filter does not separate the two types effectively, resulting in a loss of some of the cells of interest thus reducing separation efficiency. Moreover, filtering using too high of a force can cause cells to rupture.

Separation by centrifugation works well when the two types of cells are very different as in the example of the separation of white and red blood cells. But centrifugation fails when the two types of cells have similar density and size, such as white blood cells and cancer cells. A further limitation of centrifugation-based cell separation is that the density of the cells are not constant, as even dead cells react to the conditions of their surrounding and environment.

Separation by chemical properties utilizing immuno-based chemistry by antibody binding of the cell to a surface antigen (which can possibly be attached to magnetic beads) is expensive, labor-intensive, and time-consuming. Many of the steps can have cell losses thus reducing the separation efficiency of this type of method. Also, cells will be lost if they don't have the matching antigen, and/or if the antigen is obscured by other blood components. Blood plasma proteins may coat the cells in circulation (a possible method of cancer cells evading the immune system) thus preventing their recognition by the antibody. The cells separated by this method are often in a form that is difficult for a visual examination of the results.

Separation by the above methods can damage the cells both bio-chemically, and mechanically, thus changing the cell morphology, and inhibiting subsequent processing, and analysis.

Advantages

Accordingly the present invention may have one or more of the following advantages:
(a) to provide a method to separate biological objects by object type
(b) to provide a method to separate the objects by object type where the different object types can not be fully differentiated by size, shape, and density (leukocytes and certain cancer cells are two important examples)
(c) to provide a method to separate biological objects by types of object without the need to have a priori knowledge of the objects internal bio-chemistry
(d) to provide a method with high separation efficiency. Having high separation efficiency allows the use of smaller sample sizes with less chance of missing objects of interest.
(e) where minimum or no damage, both bio-chemically, and morphologically, to the objects of interest, thus not interfering with subsequent processing and analysis
(f) where the resulting objects are in a form that maintains the correct morphology
(g) where the resulting separated objects can be easily presented on a slide in a way that is preferred by a pathologist, or be read by automated vision system, or remain in a liquid solution for subsequent processing
(h) the invention may be applicable to other types of biological objects such as bacteria
(i) the invention can be used with most samples that are in solution, or that could be put in solution, and as such it is not limited to separation of objects from blood, and spinal fluids

SUMMARY OF THE INVENTION

The present invention is a method of separating a multitude of biological objects by the type of the object. The method can be applied to but is not limited to most tumor cells that might be present in a sample of blood, allowing the tumor cells to be separated from the majority of the normal blood cells.

DRAWINGS

Reference Numerals

Figure 1:
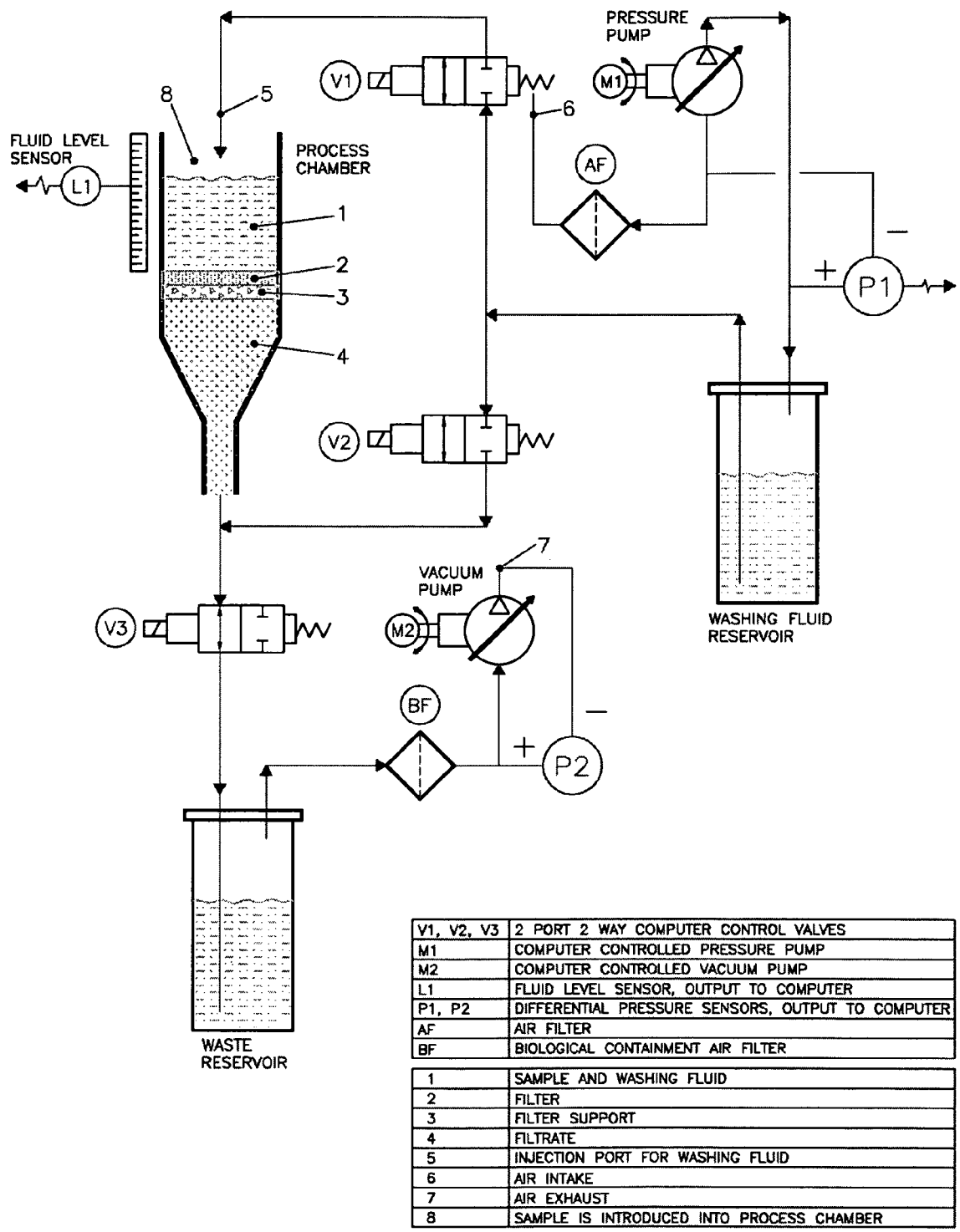
FIG. 1 is the apparatus used for implementing the method.

V1, V2, V3 are 2 port 2 way electronically controlled valves
M1 electronically controlled pressure pump
M2 electronically controlled vacuum pump
L1 Fluid level sensor, output to computer
P1, P2 Differential pressure sensors, output to the controller
AF Air filter
BF Biological contaminate air filter
1 Sample and washing fluid
2 Filter
3 Filter support
4 Filtrate
5 Injection port for washing fluid
6 Air intake
7 Air Exhaust
9 Sample is introduced into process chamber

DETAILED DESCRIPTION

Preferred Embodiment

FIG. 1 is the apparatus used for implementing the method.
1. The process chamber is divided into two sections by a barrier (filter) (2) consisting of an array of holes or pores supported by a coarse grid (3)
2. A small portion of the sample containing a suspension of different types of cells (9) is injected into the top of the chamber (1).
3. Opening (V1) injects washing fluid through injection port (5) into the top of the chamber (1).
4. Fluid Level Sensor (L1) monitors flow rate and fluid level to the controller.
5. When (V3) is opened the vacuum pump pulls fluid through the filter into the bottom of the process chamber (4) and then into the waste reservoir.
6. As the filter starts to get plugged the pressure differential across the filter increases. Because one side of the process chamber is at atmospheric pressure, the pressure differential across the filter is related to the vacuum created, and is controlled by the control computer through the use of differential pressure sensor (P2), and varying the speed of the Vacuum Pump motor (M2). The force across the filter is dynamically controlled by the controller or by a pressure regulator.
7. To process more sample, (V3) is closed and (V2) is briefly opened and then closed to back flush the filter with washing fluid, this removes any caking of the filter and prevents trapping of smaller cells.
8. Steps 2 to 7 are repeated until the complete sample is processed.
9. The enriched sample is now available on the topside of the filter.

Notes on FIG. 1:
1. Pressure Pump, M1, P1, AF are used to pressurize the washing fluid.
2. BF is used for safety to filter out any biohazard from the exhaust (7).
3. The washing fluid should be of a type that preserves the morphology of the cells; in this case it was from 10 to 70 percent ethanol.

DETAILED DESCRIPTION

Concepts

Figure 2:
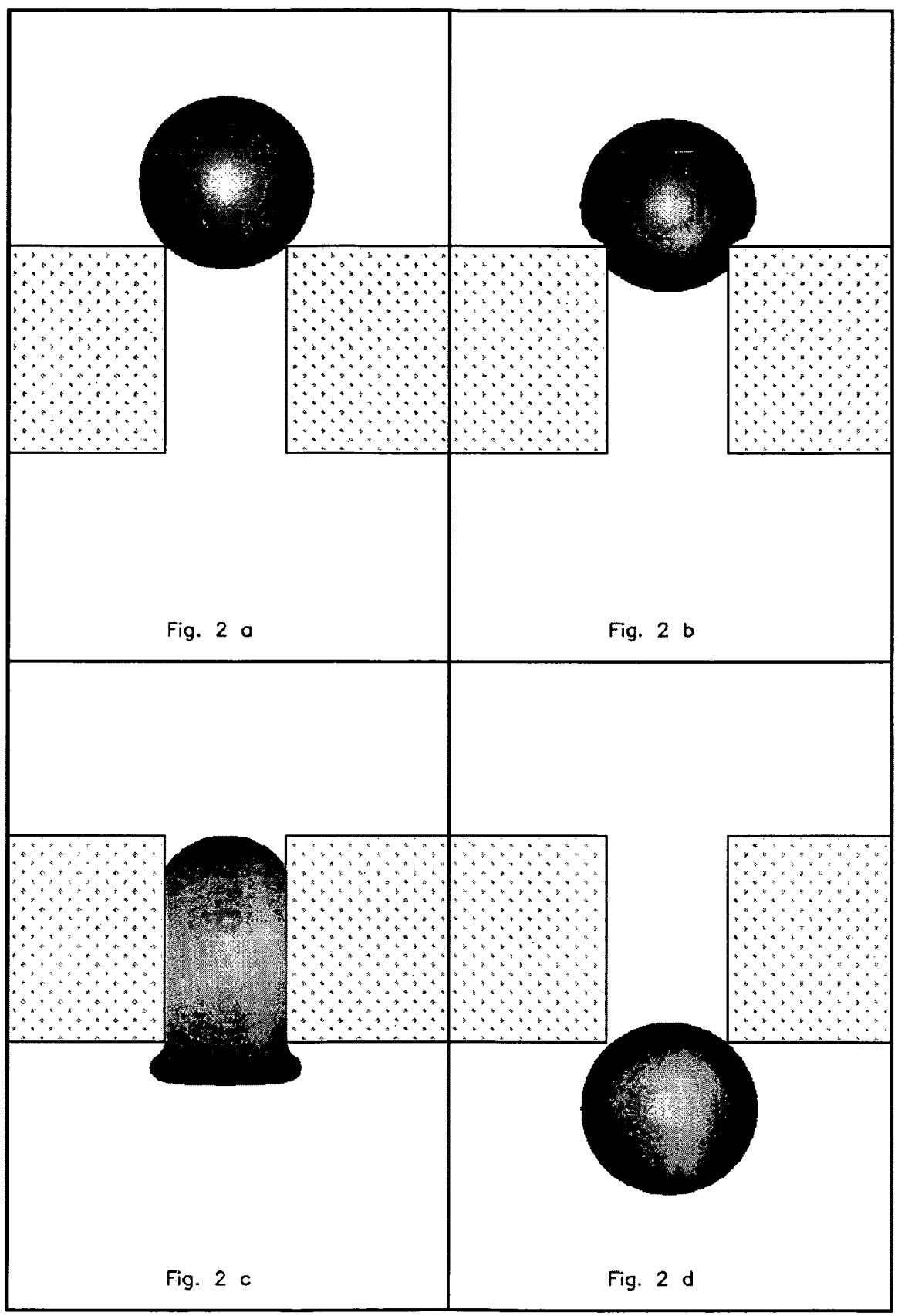
FIG. 2-a, 2-b, 2-c, 2-d are closely related conceptual drawings of a cell being forced through a smaller hole by the pressure differential.

FIG. 2-a, 2-b, 2-c, 2d are conceptual drawings of a cell being forced through a smaller hole by the pressure differential.
a) Cell is attracted to empty hole by fluid flow through the hole. (higher pressure on the top) FIG. 2-a
b) Pressure differential starts to deform and fold cell pushing it into the hole. FIG. 2-b
c) Cell is pushed through the hole by pressure differential FIG. 2-c
d) Cell is expelled away from the hole by fluid flow through the hole FIG. 2-d The force (pressure differential) needed to push the cell through the smaller hole is dependent on size and the viscoelastic properties of the cell. Viscoelastic properties of an object are the properties that allow the object to elastically fold, and to bend, and to distort their shape, and to flow through holes and passageways that are of smaller then the object. Literature indicates that the white blood cells (leukocytes) have relatively high viscoelastic properties; this allows them to flow through small diameter passageways and reach tissues via the body's microscopic blood vessels.

Tumor cells can be of a similar size to that of white blood cells. But tumor cells are found to have considerably lower viscoelastic properties. Hence a tumor cells needs considerably more force to push it through a small diameter hole as compared to a white blood cell of a similar size. The tumor cells will be stopped by the small hole size and will not go past the point in FIG. 2-a. Exploiting this difference in the viscoelastic properties of the two cell types enables the cells to be separated by type. Sorting cells by utilizing this property is a unique method and the basis of this invention.

Figure 3:
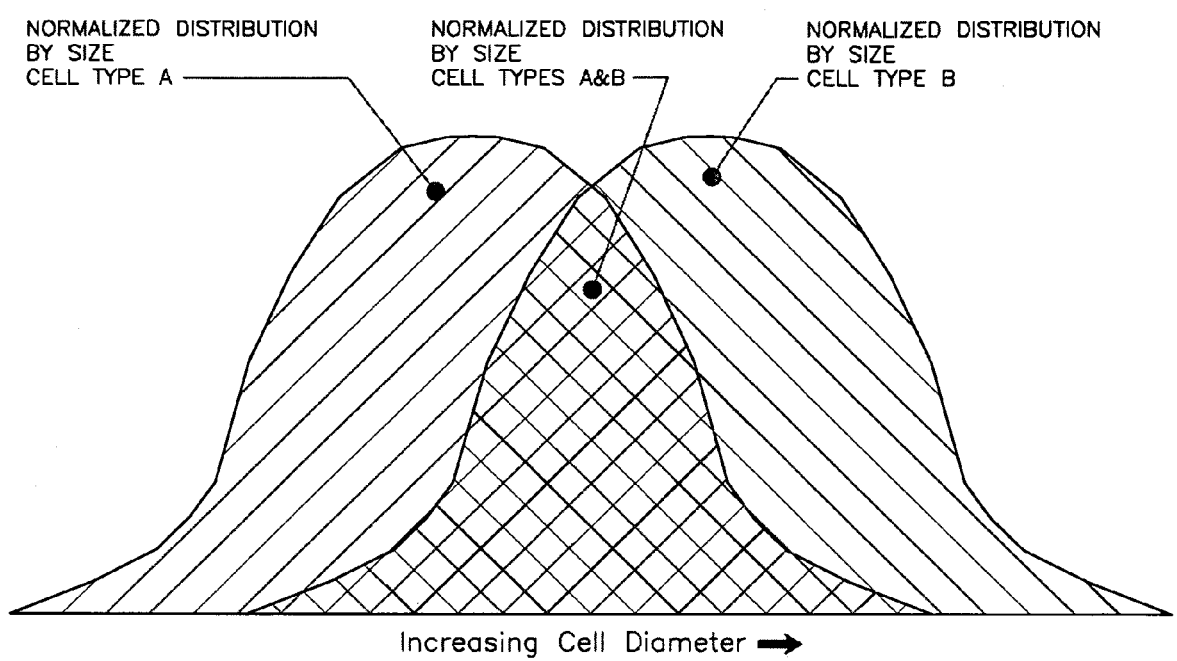
FIG. 3 is a representation of the overlap in normalized size distributions of two cell types.

FIG. 3 is a representation of the overlap in normalized size distributions of two cell types. A primary example of the use of this invention is for the separation of separating tumor cells (cell type B) from white blood cells (leukocytes) (cell type A). 5 ml of whole peripheral blood has approximately 25 million white blood cells (leukocytes). The concentration of cell type B to that of cell type A could be as low as 0.2 parts per million. The size distribution for both cell types has a large amount of overlap.

Figure 4:
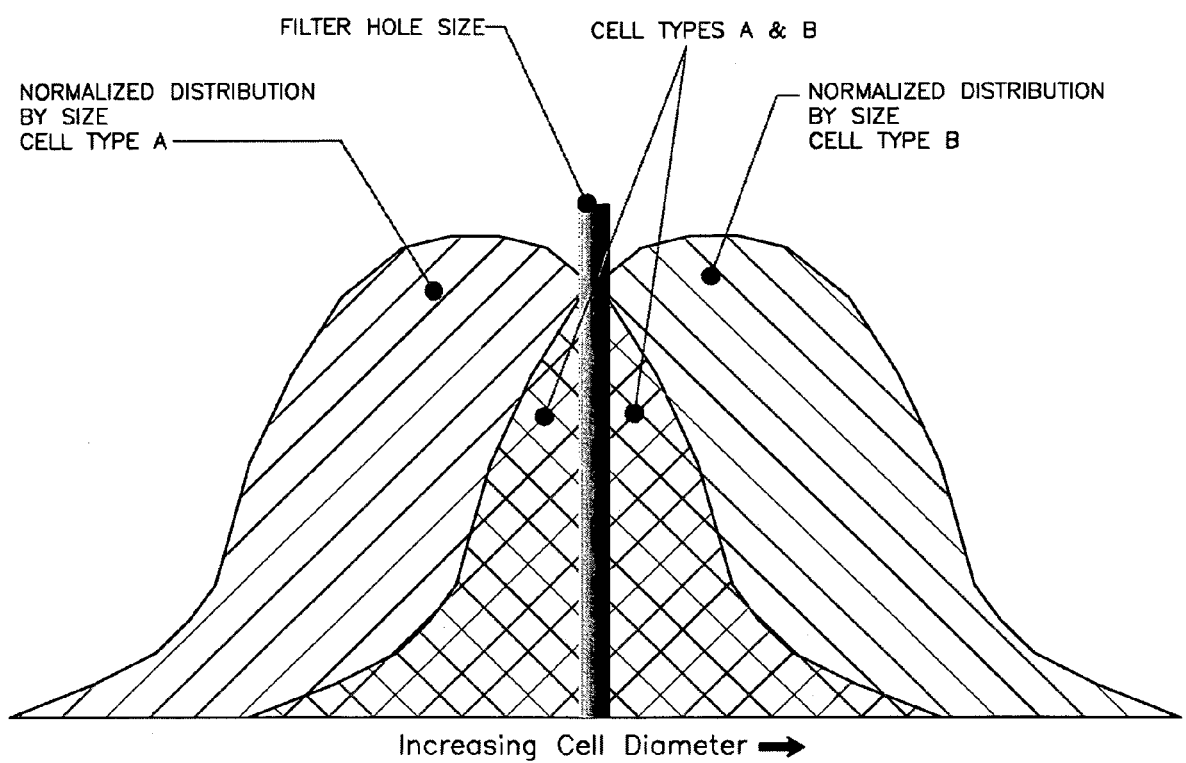
FIG. 4 indicates the conventional separation of the two cell types from FIG. 3 by a filter with a fixed hole or pore size.

FIG. 4 indicates the conventional separation of the two cell types from FIG. 3 by a filter with a fixed pore or hole size. Cells with sizes smaller then the filter pore hole size (left side of filter) will be separated from those on the right side. Note the large amount of overlap on both sides of the filter for the two types of cells. With a smaller hole size, a larger amount of type A cells remain with the type B cells, thus reducing the concentration of the cells of interest (cell type B). Conversely with a larger hole size, more type B cells (the cells of interest) are lost, reducing overall sensitivity to type B cells. Also, the position and shape of the distribution curves will vary from patient to patient. It is because of this overlap and variation in distribution that conventional filtering by size does poorly on the separation of the two cell types.

Figure 5:
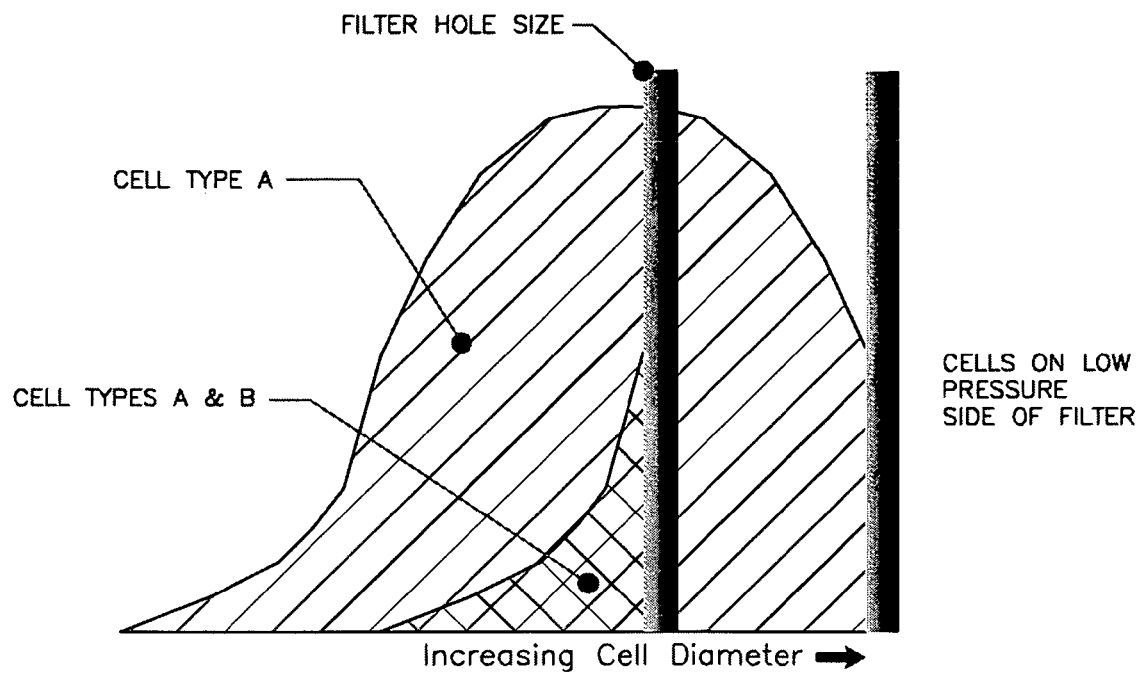
FIG. 5-a and 5-b are closely related drawings representing the efficacy of this invention for improving recovery and enrichment of the cells of interest using a controlled pressure differential to separate the two types of cells.
Figure 5:
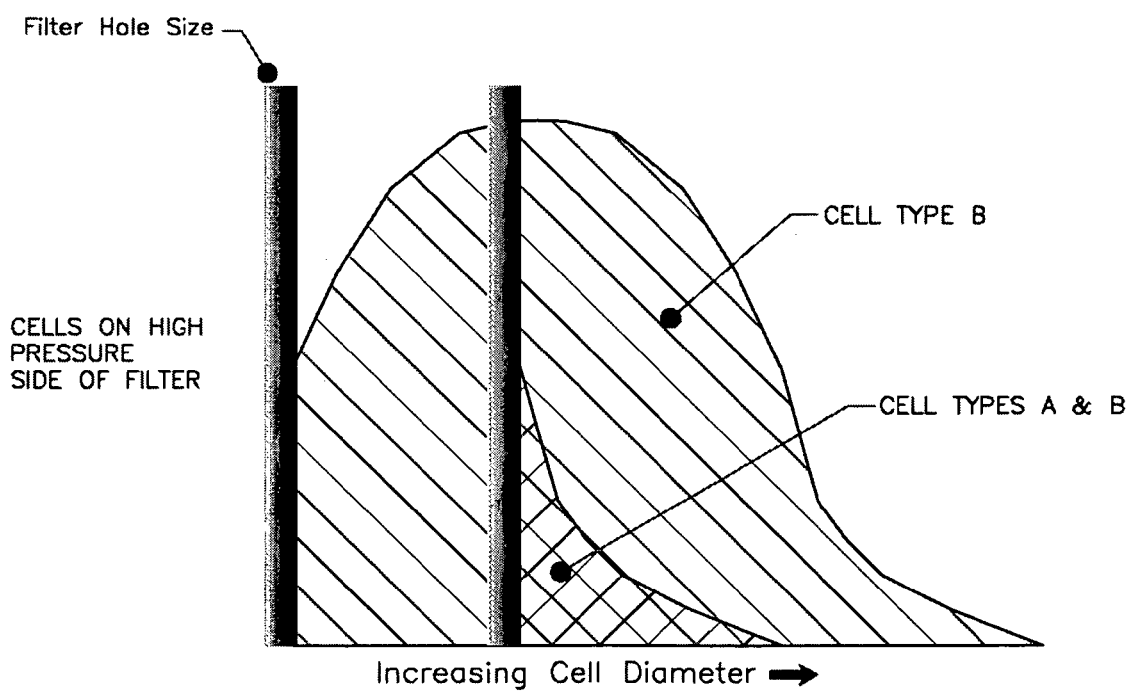

FIG. 5-*a* and 5-*b* represents the efficacy of this invention for improving recovery and enrichment of the cells of interest using a controlled pressure differential to separate the two types of cells. Cells of type A even when they are larger then the hole (pore) size of the filter will pass through because of their higher viscoelastic properties as compared to type B cells (FIG. 5-*a* low-pressure side of filter). Type B cells will not get through the filter unless the cell size is less than or close to the pore size of the filter (FIG. 5-*b* high-pressure side of filter).

Notice that, compared to conventional filtering (FIG. 4); on both sides of the filter there is only a small amount of overlap of the two types of cells.

Eight microns is smaller then the diameter of most types of tumor cells. For an 8 micron pore size, and cell type A being leukocytes, a range of force around a maximum of 10 lbs/in2 was predetermined by experiment to be adequate to force the majority of leukocytes to pass through the filter pores without passing, or damaging the majority of tumor cells.

Forces that are too high or that are uncontrolled, like those associated with standard filtering, can cause cells to rupture.

Figure 6:
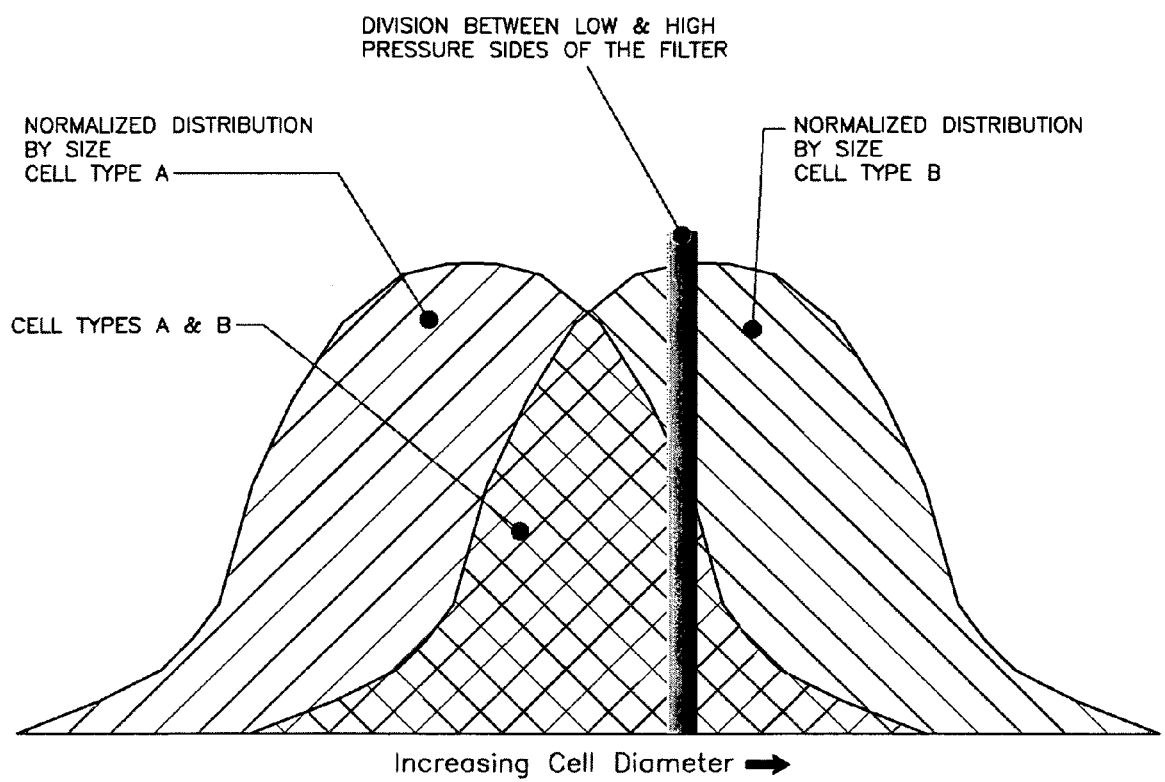
FIG. 6 indicates the decreased separation efficiency that is observed when using a pressure differential that is too high.

FIG. 6 indicates the decreased separation efficiency that is observed when using a pressure differential that is too high. As the pressure differential is increased, cells of type B pass through the pores to the low-pressure side of the filter, decreasing the recovery of type B cells. In addition too high a pressure could cause cell damage, or even bursting.

Figure 7:
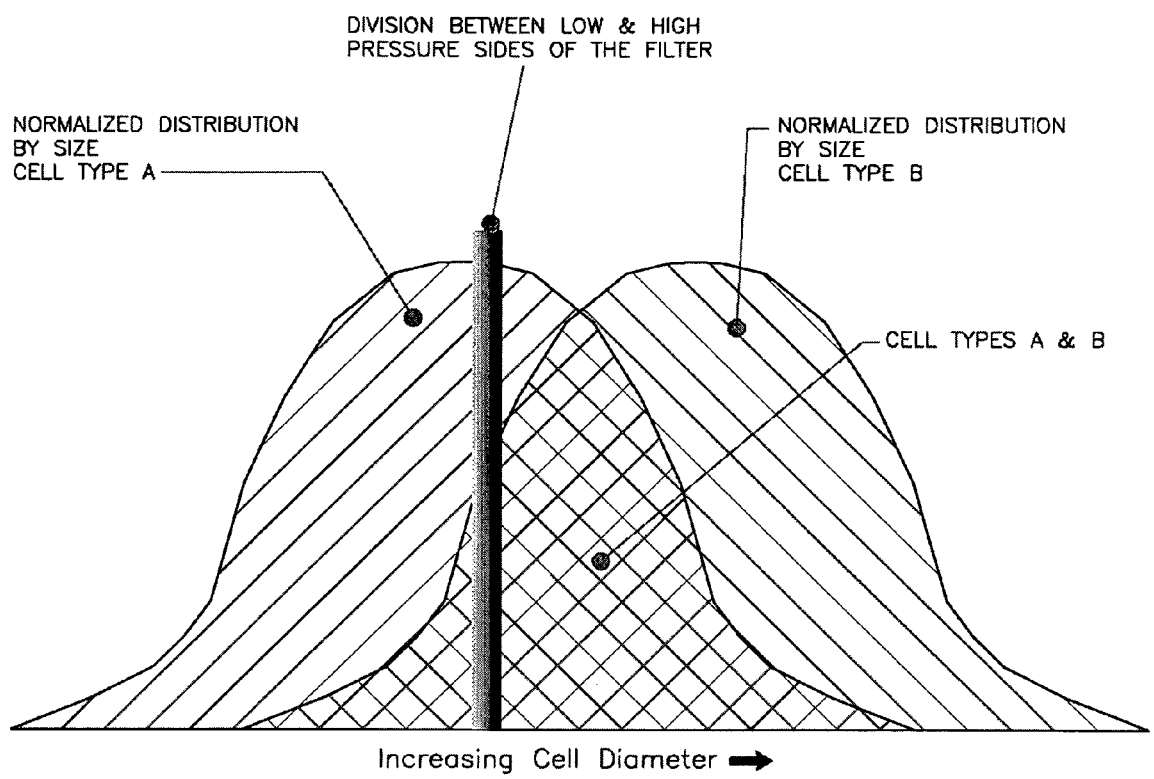
FIG. 7 indicates the decreased separation efficiency that is observed when using a pressure differential that is too low.

FIG. 7 indicates the decreased separation efficiency that is observed when using a pressure differential that is too low. As the pressure differential is decreased, only those cells that are smaller then the filter pore size will pass through to the low-pressure side of the filter. In this case cell selection approaches conventional filtering. This decreases the sensitivity for removal of type A cells, increases the number of type A cells mixed in with type B cells, thus decreasing the concentrated enrichment of the cells of interest.

DETAILED DESCRIPTION

Alternative Embodiments of the Apparatus in FIG. 1

1. An equally effective system could use a closed process chamber and pressure or direct displacement instead of vacuum to create the controlled force across the filter.
2. Similarly the differential pressure sensor can be relocated to other locations or replaced with force sensors or equivalent sensors, the only requirement being that the differential forces across the filter are controllable.
3. If the cells in the waste reservoir are of interest they can be easily extracted from waste fluid.
4. The method could be repeated as many times as was useful on the enriched sample from the previous enrichment cycle. Each repeat would use the same apparatus or a copy of the apparatus with a different filter hole size, and a different range of forces.

CONCLUSION, RAMIFICATIONS, AND SCOPE

Accordingly the reader will see that a method has been provided by this invention that will separate biological objects by object type. The method will separate the objects by object type even when the different object types can not be fully differentiated by size, shape, and density and chemistry. The separation of leukocytes from certain cancer cells is an important example of this case.

The method is not limited to a liquid biological sample. As an example a solid tissue biopsy can be preprocessed to break the tissue down into individual cells. The cells can then be suspended in a preservative fluid.

While the above description contains many specificities, these should not be construed as limitations on the scope of the invention, but as exemplifications of the presently preferred embodiments thereof. Many other ramifications and variations are possible within the teachings of the invention. For example, the process chamber could be closed or open, and could be of any shape or size. Thus the scope of the invention should be determined by the appended claims and their legal equivalents, and not by the examples given.

The invention claimed is:

1. A method of separating a multitude of biological objects, comprising:
    (a) each of the biological objects belong to one of at least two types of cells,
    (b) at least one of the types of cells has the property of having lower viscoelastic properties than the remaining types of cells, for clarity the objects having lower viscoelastic properties will be labeled the low viscoelastic objects, and the remaining objects will be labeled the high viscoelastic objects,
    (c) said biological objects if not already in a fluid are suspended in a fluid,
    (d) a first means for providing a chamber for holding the fluid,
    (e) a second means for providing a barrier,
    (f) said barrier has a plurality of holes of approximately equal to a predetermined diameter,
    (g) said diameter is chosen to be smaller than the majority of the low viscoelastic objects,
    (h) said chamber is separated by the barrier into an input side, and an output side of the chamber,
    (i) a third means to introduce said fluid into the input side of the chamber,
    (j) a fourth means for applying a controlled force to said fluid,
    (k) said controlled force kept lower than the predetermined force needed to force a majority of the low viscoelastic objects through the holes,
    (l) said controlled force is higher than the predetermined force needed to force a majority of the high viscoelastic objects through the holes,
    (m) said controlled force is applied to the fluid, thereby forcing the fluid, and the majority of the high viscoelastic objects to flow through the plurality of holes to the output side of the chamber,
    (n) whereby the majority of the low viscoelastic objects remain on the input side of the chamber, and the majority of the high viscoelastic objects have flowed through to the output side of the chamber, thereby separating the majority of the high viscoelastic objects from the majority of the low viscoelastic objects,
    wherein the biological objects are leukocytes and tumor cells.

2. The method of claim 1 wherein in addition to the fluid introduced by the third means an additional type of fluid can be added before, during, and after the fluid is introduced by the third means into the input side of the chamber.

3. The method of claim 1 wherein the separated biological objects can be further separated by repeating the method using a different predetermined force, and a different predetermined diameter.

* * * * *